United States Patent
Bransgrove

(10) Patent No.: US 11,491,481 B2
(45) Date of Patent: Nov. 8, 2022

(54) DIAGNOSTIC TEST UNIT FOR ANALYSING BODY FLUID

(71) Applicant: Brandon Bransgrove, Gordon (AU)

(72) Inventor: Brandon Bransgrove, Gordon (AU)

( * ) Notice: Subject to any disclaimer, the term of this patent is extended or adjusted under 35 U.S.C. 154(b) by 74 days.

(21) Appl. No.: 16/610,240

(22) PCT Filed: Jun. 2, 2018

(86) PCT No.: PCT/AU2018/050550
§ 371 (c)(1),
(2) Date: Nov. 1, 2019

(87) PCT Pub. No.: WO2018/218311
PCT Pub. Date: Dec. 6, 2018

(65) Prior Publication Data
US 2021/0106988 A1    Apr. 15, 2021

(30) Foreign Application Priority Data

Jun. 2, 2017    (AU) .............................. 2017-902117
Feb. 3, 2018    (AU) .............................. 2018-900335

(51) Int. Cl.
*B01L 3/00*        (2006.01)
*G01N 33/487*    (2006.01)
*G01N 35/00*      (2006.01)

(52) U.S. Cl.
CPC ...... *B01L 3/5027* (2013.01); *G01N 33/48764* (2013.01); *G01N 35/00009* (2013.01); *G01N 2035/00019* (2013.01)

(58) Field of Classification Search
CPC ............ B01L 3/5027; G01N 33/48764; G01N 35/00009; G01N 2035/00019; A61B 5/15;
(Continued)

(56) References Cited

U.S. PATENT DOCUMENTS

| 1,947,376 A | 2/1934 | Burrell |
| 1,965,812 A | 7/1934 | Winsor |
(Continued)

FOREIGN PATENT DOCUMENTS

| GB | 846780 A | 8/1960 |
| WO | 2013/040630 A1 | 3/2013 |

OTHER PUBLICATIONS

Engineers Edge (Spring Steel Review, Engineers Edge Solutions by Design, 2015, 1 page (Year: 2015).*

(Continued)

*Primary Examiner* — Benjamin R Whatley
*Assistant Examiner* — Jean Caraballo-Leon
(74) *Attorney, Agent, or Firm* — Oliff PLC

(57) ABSTRACT

A diagnostic tester for analysing a body fluid includes a test tape having test zones configured to receive the body fluid. The tester further includes a chamber configured to contain the test tape and a seal. The tester further includes an opening of the chamber which is at least partially bordered by the seal. The tester further includes a face on the chamber that borders the opening, at least part of the face being formed by the seal. The tester further includes a closing leaf spring sealed onto the face, the closing leaf spring shielding the opening from an environment outside the chamber. The tester further includes an exit gap formed between the closing leaf spring and the seal through which the test tape is configured to exit the chamber.

19 Claims, 5 Drawing Sheets

(58) Field of Classification Search
CPC ........ A61B 5/150358; A61B 5/150022; A61B 5/150305; A61B 2560/0431; B65H 18/103; B65H 2701/37; B65H 2701/1942; B65H 18/145; B65D 85/672
See application file for complete search history.

(56) References Cited

U.S. PATENT DOCUMENTS

| | | |
|---|---|---|
| 1,989,912 A | 2/1935 | Breuer |
| 1,991,126 A | 2/1935 | Stevenson |
| 2,040,638 A | 5/1936 | Beck |
| 2,161,230 A | 6/1939 | Nelson |
| 3,342,318 A | 9/1967 | Ruekberg |
| 3,728,081 A * | 4/1973 | Bidanset .......... G01N 35/00009 422/66 |
| 4,988,016 A | 1/1991 | Hawkins et al. |
| 5,077,010 A | 12/1991 | Ishizaka et al. |
| 6,050,435 A | 4/2000 | Bush et al. |
| 6,079,594 A | 6/2000 | Brown et al. |
| 7,582,258 B2 | 9/2009 | Ruhl et al. |
| 8,187,537 B2 | 5/2012 | Sacherer et al. |
| 8,187,538 B2 | 5/2012 | Jakubowicz et al. |
| 2005/0232815 A1 | 10/2005 | Ruhl et al. |
| 2007/0151884 A1 | 7/2007 | Thoes et al. |
| 2009/0098644 A1* | 4/2009 | Sacherer .......... G01N 33/48764 435/287.7 |
| 2010/0198109 A1 | 8/2010 | Harttig |
| 2014/0054190 A1* | 2/2014 | Bransgrove ............ B65D 85/67 206/409 |
| 2015/0202619 A1* | 7/2015 | Bransgrove ...... G01N 33/48764 422/401 |
| 2018/0312290 A1 | 11/2018 | Uchihashi et al. |
| 2019/0026616 A1 | 1/2019 | Bourque et al. |
| 2019/0351351 A1 | 11/2019 | Singh |

OTHER PUBLICATIONS

Real Seal (Rubber vs TPE—which is the better choice?, Real Seal Website, 2012, 1 page (Year: 2012).*
Aug. 9, 2018 International Search Report issued in International Patent Application No. PCT/AU2018/050550.
Aug. 9, 2018 Written Opinion issued in International Patent Application No. PCT/AU2018/050550.

* cited by examiner

DIAGNOSTIC TEST UNIT FOR ANALYSING BODY FLUID

FIELD

The invention relates to a diagnostic test unit for analysing body fluid, in particular but not exclusively, a diagnostic test unit for analysing body fluid such as blood, interstitial fluid and urine.

BACKGROUND

Portable analysis of body fluids such as blood, interstitial fluid, urine etc. is commonly undertaken using disposable tests. These tests must be stored in a desiccated state until use to preserve the reagents and so maximise shelf life. Some storage containers are required which allow the removal of tests without a lid being opened and closed by the user, for example those found in cassettes and magazines that hold test tape or test strips.

U.S. Pat. No. 5,077,010 to Ishizaka et al describes a cassette housing, transparent carrier tape with information fields and test fields for diagnostic use. Humidity is kept out of the unused tape chamber by means of a flexible gasket or a series of flexible gaskets. The unused tape is preserved by the seal for several days only. U.S. Pat. No. 7,582,258 to Ruhl et al describes a cassette with a hydraulic sealing means used to prevent moisture entering the unused test chamber. The said sealing means is inflated by downward pressure applied by a stamp, this causes the sealing means to press directly onto the carrier tape sealing it against the cassette. That patent also describes a seal similar to that of U.S. Pat. No. 5,077,010, but with two gaskets inclined in opposite directions to one another. U.S. Pat. No. 8,187,538 to Sacherer et al describes a container, heat sealed closed with an aluminium foil lid. The tape exits from an area where there is a TPE (thermoplastic elastomer) seal under the foil. A leaf spring is used to press the closing foil onto the seal and so create a barrier. Securing the spring reliably and ensuring the foil is pressed evenly is critical for this solution to work.

OBJECT

It is an object of the present invention to provide a diagnostic test unit for analysing body fluid which addresses or at least ameliorates the above drawbacks of the prior art or provides a useful alternative.

SUMMARY

According to a first aspect there is disclosed a diagnostic test unit for analysing a body fluid, the test unit including (i) a test tape having test zones for receiving the body fluid, and (ii) a chamber for containing the test tape, wherein the chamber defines an opening which is at least in some sections bordered by a seal, the opening being shielded from an environment outside the chamber by a closing leaf spring sealed onto a face on the chamber bordering the opening, at least one section of the face being formed by the seal and test tape operatively exits the chamber through an exit gap formed between the closing leaf spring and the seal.

Preferably a roll of test tape is installed through the opening into the chamber.

Preferably the test tape includes (i) a carrier tape with test zones spaced at intervals, and (ii) a test zone free area of carrier tape which is located in the exit gap during storage.

Preferably the chamber is part of a cassette, the test tape adapted to be moved out of a storage chamber via an application site into a waste chamber, the exit gap being located proximate the storage chamber.

Preferably the seal and leaf spring seal against the test tape.

Preferably a rear side of test tape facing away from a test field operatively slides over the seal.

According to a second aspect there is disclosed a diagnostic test unit for analysing a body fluid, the diagnostic test unit including (i) multiple test strips, each test strip having at least one test zone for receiving body fluid, and (ii) a chamber for containing the test strips, wherein an opening of the chamber is at least in some sections bordered by a seal, the opening being shielded from an environment outside the chamber by a closing leaf spring, the closing leaf spring being sealed onto a face on the chamber bordering the opening, at least one section of the face being formed by the seal and wherein test strips exit the chamber through an exit gap formed between the closing leaf spring and the seal.

Preferably the test strips are installed into the chamber through the opening.

Preferably the chamber is part of a magazine wherein test strips are adapted to be transported out of the chamber to an application site.

Preferably when the closing leaf spring is applied, the gap formed.

Preferably the closing leaf spring is joined along a sealing line with the chamber and/or the seal.

Preferably the closing leaf spring is produced from spring steel having a heat-seal coating.

Preferably the seal is either (i) a single component injection-moulded part or (i) in combination with the chamber as a co-moulded part formed from TPE (thermoplastic elastomer).

According to a third aspect there is disclosed a diagnostic test unit for analysing a body fluid including (i) a test tape provided with test fields for applying the body fluid, and (ii) a chamber for containing the test tape, wherein an opening of the chamber is at least in some areas bordered by a seal, the opening (i) being shielded from an environment outside the chamber by a closing leaf spring and (ii) acting as a passageway for installing components of the chamber before the closing leaf spring is applied, in use test tape passing through a gap formed between the closing leaf spring and the seal.

According to a fourth aspect there is disclosed a diagnostic test unit for analysing a body fluid, the diagnostic test unit including (i) multiple test strips, each with at least one test zone for receiving body fluid, and (ii) a chamber containing the test strips, wherein an opening of the chamber is at least in some sections bordered by a seal, the opening being shielded from an environment outside the chamber by a closing leaf spring, the closing leaf spring being sealed onto a face on the chamber bordering the opening wherein at least one section of the face is formed by the seal, test strips operatively exit through a gap formed between the closing leaf spring and the seal, the opening adapted to allow components of the chamber to be installed before the closing leaf spring is applied, wherein test strips are transported out of the chamber to an application site through a gap formed between the closing leaf spring and the seal.

According to a fifth aspect there is disclosed a portable device for analysing a body fluid, the device including a receiving bay to load a diagnostic test unit, the test unit including (i) multiple test strips, each with at least one test zone for receiving body fluid and (ii) a chamber containing the test strips, wherein an opening of the chamber is at least in some sections bordered by a seal, the opening being shielded from an environment outside the chamber by a closing leaf spring, the closing leaf spring being sealed onto a face on the chamber bordering the opening, at least one section of the face being formed by the seal, wherein test strips exit to an application site through a gap formed between the closing leaf spring and the seal, the opening adapted to allow components of the chamber to be installed before the closing leaf spring is applied.

Preferred embodiments utilise a leaf spring in combination with a seal located in at least one section of a supply chamber opening, to shield the test tape or test strips stored in the supply chamber, from the environment outside the chamber. The leaf spring is applied directly over the opening of the storage chamber, closing it to the outside environment, after the chamber has been loaded with test tape or test strips and drying agent. The closing leaf spring is sealed onto a face on the chamber which borders the opening and at least one section of the face is formed by a seal. The test tape or strips exit through a gap between the closing leaf spring and the seal. The gap can be formed by laying the start of the tape roll across the seal before the closing leaf spring is applied. The tape may then be drawn out of the chamber over the seal and under the leaf spring. When a test zone, which is thicker than the carrier tape, exits the chamber, the leaf spring flexes allowing the height of the gap to increase to make room for the test zone. After the test zone has cleared the seal the leaf spring resumes its lower position, where the seal and the leaf spring seal against the test tape.

The leaf spring may be applied to the face that borders the chamber opening, using any suitable method for ensuring a tight fit. It may be heat staked, heat welded or ultrasonically welded directly onto the face.

In a preferred embodiment the invention utilises a leaf spring laminated with a heat seal material, for example a cast polypropylene (CPP). The cassette chamber is constructed from a material that is compatible with the heat seal material, for example polypropylene (PP). In at least one area the chamber opening has a seal where the tape exits. After loading the cassette tape, the storage chamber is closed by covering it with the leaf spring which is then heated to melt the heat seal layer to the cassette opening. The heat seal layer can be welded to the seal as well as the face bordering the opening. The test tape comprises a PET carrier tape with test zones located at intervals. When the leaf spring is welded to the face that borders the chamber opening it does not weld to the carrier tape as it is formed from a material that is not compatible with the heat seal layer, for example Polyethylene terephthalate (PET). The spring can be formed from any material that is flexible and returns to its original shape after deflection. A material with a very low water vapour transmission rate (WVTR) such as spring steel is ideal. It is possible however to use a material that has a good spring force but high WVTR if the spring material is then laminated with a barrier film such as a PET with various coatings for example a SiOx coating (WVTR<0.1 g/m2/24 hours at 37.8 C 85% RH). The tape exits over a seal formed into the rim of the chamber. The seal can be formed from a TPE (thermoplastic elastomer) that is co-moulded with the cassette housing. A very soft TPE (Shore A<50) is preferred to improve the seal around the tape.

Once the leaf spring is bonded in position, it provides downward pressure on the tape at the point where it exits the chamber over the seal. The spring exerts sufficient force to maintain a seal, while also being capable of flexing to rise and fall to allow the passage of a test zone through the seal. This is particularly desired for battery powered devices that must pull the tape and test zones through the seal. Seals that are too tight can stall a motor or drain a battery prematurely. The height of the TPE seal relative to the rim, can be adjusted to modify the spring force applied to the tape at the exit.

BRIEF DESCRIPTION OF THE DRAWINGS

Preferred embodiments of the present invention will be described hereinafter, by way of examples only, with reference to the accompany drawings, wherein.

DESCRIPTION OF PREFERRED EMBODIMENTS

Figure 1:
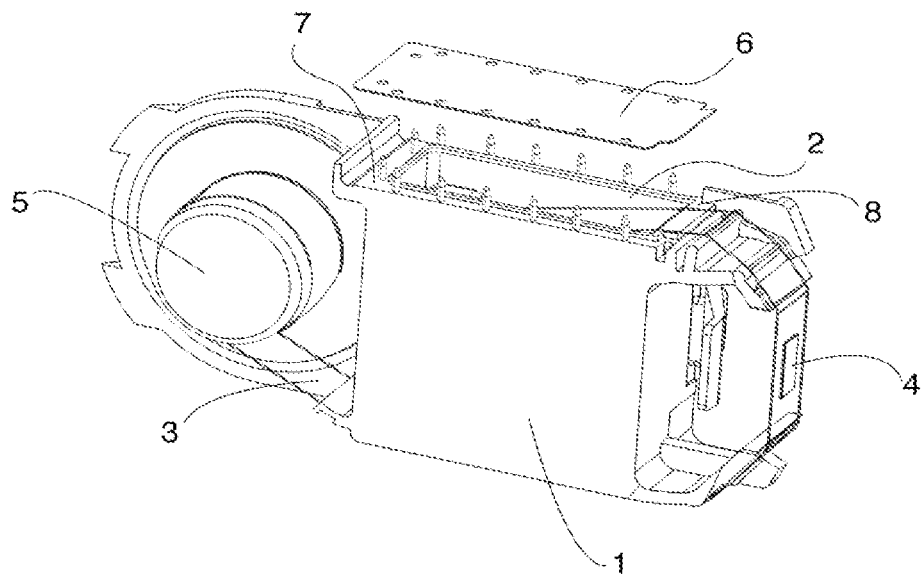
FIG. 1 is a schematic perspective view of a first embodiment diagnostic test unit for analysing body fluid.

In order to convey the concepts of preferred embodiments of the invention, reference will now be made to embodiments illustrated in the drawings and described herein. It is important to understand that no limitation to the scope of the invention is intended, and variations, modifications and further applications of the principles of the invention shown in the figures is contemplated as would normally be expected by a person who is skilled in the art relating to the invention. Several embodiments of the invention are shown in great detail, nevertheless some facets which are not relevant to the invention are omitted for the purpose of aiding understanding.

FIG. 1 depicts a storage chamber (2) located in a housing (1) with carrier tape (3) exiting over the top of a seal (8) that forms a ring around the opening to storage chamber (2). The carrier tape (3) is drawn from the storage chamber (2) by a drive (5) which can be either motor driven or hand turned, until a test zone (4) is over a reading head (not shown) where a sample is applied for analysis. Spring lid (6) is shown before being secured against a face (7) that borders the opening to storage chamber (2). Face (7) occupies a plane that lies below the top surface of the seal (8). The distance between the two planes is fixed by the mould that makes the co-moulded parts (housing and seal).

Figure 2:
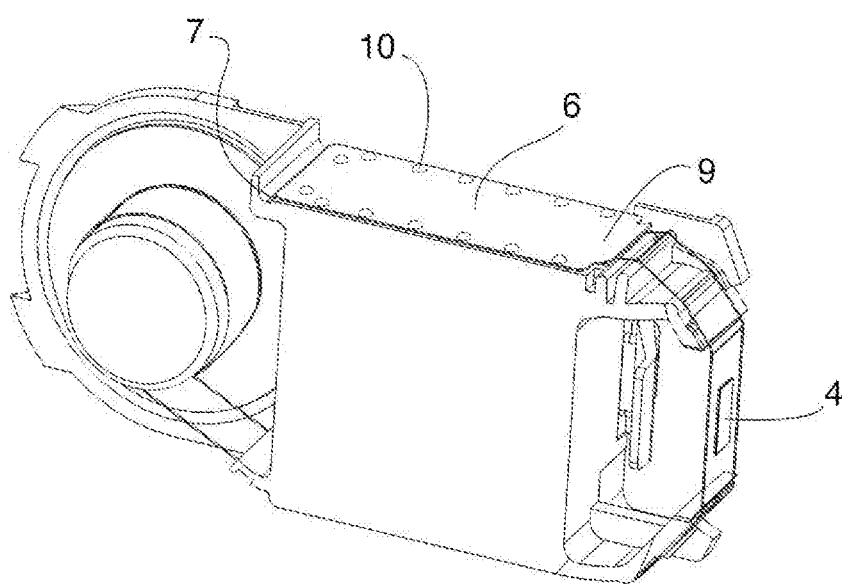
FIG. 2 is a further schematic perspective view of the diagnostic test unit of FIG. 1.

FIG. 2 shows spring lid (6) secured after loading a roll of carrier tape and a desiccant into the storage chamber. FIG. 2 shows spring lid (6) secured in position against face (7) by plastic rivets (10) that have been melted by a heat staking machine. Downward force is applied to spring lid (6) during heat staking causing it to contact face (7). Once the melted rivets have cooled the downward force is released. Spring lid (6) is held securely all around face (7) except at the tape exit area (9) where the spring is free to rise and fall as a test zone (4) exits. Despite being a thin sheet of metal, the spring lid does not transmit water vapour and provides a shield against water ingress into the chamber, whilst occupying very little space in the assembly. Seal (8) can be a TPE (thermoplastic elastomer) that is co-moulded with the housing. A very soft TPE (Shore A<40) is preferred to improve the seal around the tape as it exits via a gap formed between the leaf spring and the seal.

Strengthening ribs (not shown) may be embossed into spring lid (6) to increase its strength and maintain flatness. A groove for the seal may also be added. It can be seen that the spring lid is located in a set position against face (7) which allows a specific spring force to be applied against the seal. Moving the rivets closer to the tape exit (9) can increase the spring force as can changing the thickness of the metal spring.

Figure 3:
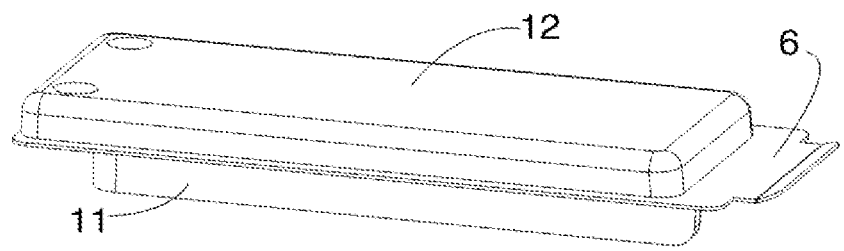
FIG. 3 is a schematic perspective view of a second embodiment diagnostic test unit for analysing body fluid.

FIG. 3 shows another embodiment of the invention. Here the spring lid (6) has plastic moulded over it to enable it to be ultrasonically welded against the rim of the opening (7 not shown). Before welding, a plastic edge (11) meets a sacrificial edge inside the chamber opening (17 not shown) preventing the spring lid from resting on face (7). An ultrasonic welding head is pressed against the top surface (12) transmitting waves of energy that cause the plastic surfaces to vibrate, heat and melt together, forming an air-tight weld. As the plastic surfaces melt the spring lid moves downwards, eventually resting flat on a face that borders the compartment opening (7).

Figure 4:
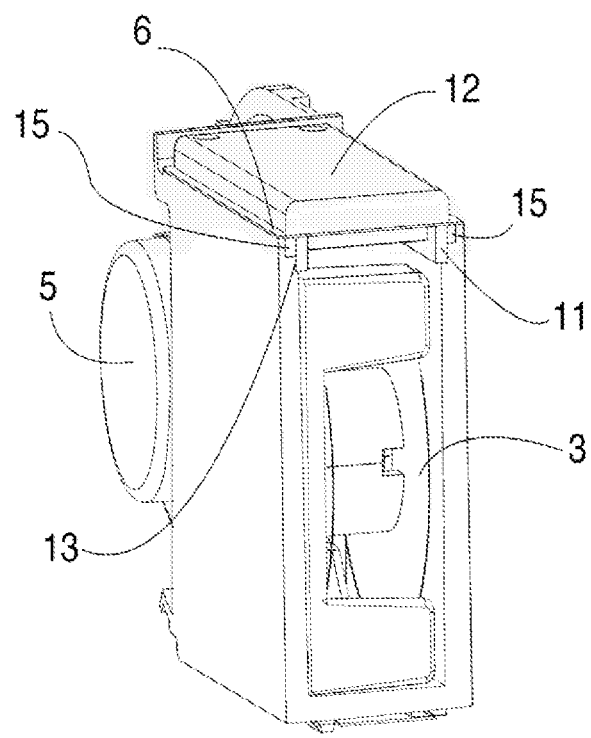
FIG. 4 is a schematic cross-sectional view of a spring lid of the diagnostic test unit of FIG. 3.

FIG. 4 shows a cross section through the ultrasonically welded spring lid (6). Plastic edge (11) has melted against the inside of the storage chamber resulting in a weld that continues all around the rim to weld point (13). Spring lid (6) rests on the rim of the opening (7) and also presses onto the seal (15) which in this example only extends across the tape exit area, where there has been no ultrasonic welding.

Figure 5A:
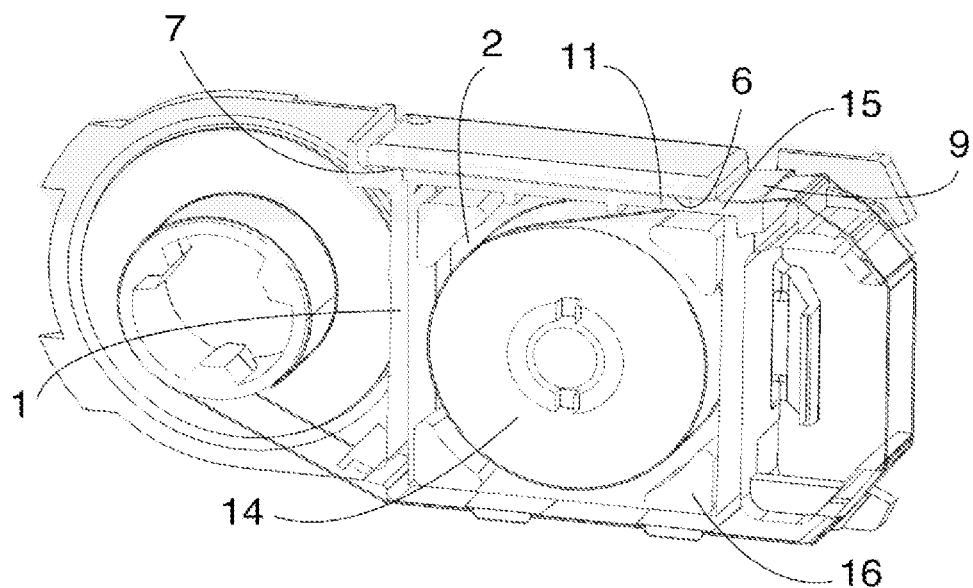
FIG. 5a is a cross-sectional view of a housing and storage chamber of the diagnostic test unit of FIG. 3 after ultrasonic welding.

FIG. 5*a* shows a cross section of the housing (1) and storage chamber (2) after ultrasonic welding. Spring lid 6 is resting on a face bordering the opening to the chamber (7) which puts it in the correct plane in relation to the top of the seal (8—not visible). This causes flexing of the spring at the tape exit area (9) creating a seal which sandwiches the tape (3) between the seal (15) and the spring lid (6) keeping moisture out of the storage chamber (2) that holds desiccant (16) and unused test tape (14).

Figure 5B:
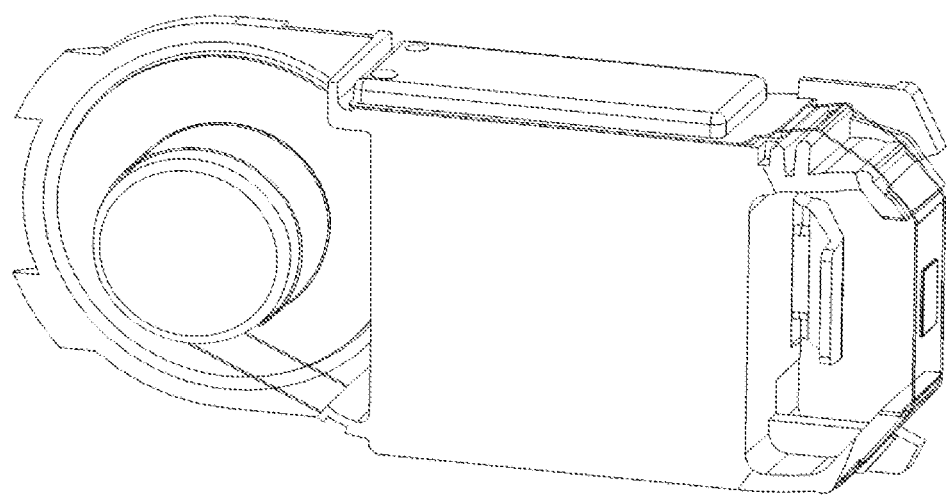
FIG. 5b is a schematic perspective view of the diagnostic test unit of FIG. 5a after the spring lid has been welded into position.

FIG. 5*b* shows the test chamber and housing with spring lid welded into position.

Figure 5C:
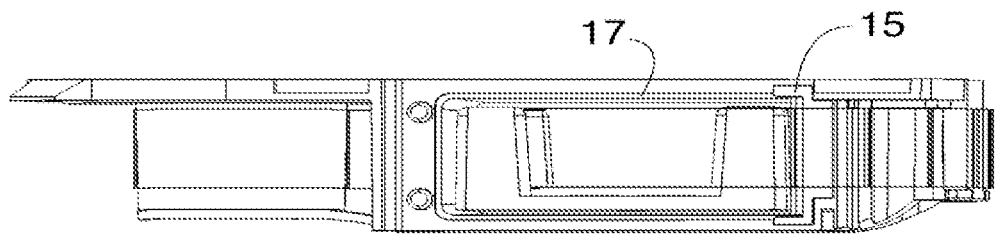
FIG. 5c is a schematic top view of a chamber of the diagnostic test unit for of FIG. 3 before ultrasonic welding.

FIG. 5*c* shows a top view of a chamber before ultrasonic welding. The seal (15) forms only a section of the face bordering the chamber opening and can be seen extending underneath the tape. Interference (17) in the form of a ledge borders the opening from one end of the seal around the chamber opening to meet the other end of the seal.

Figure 6:
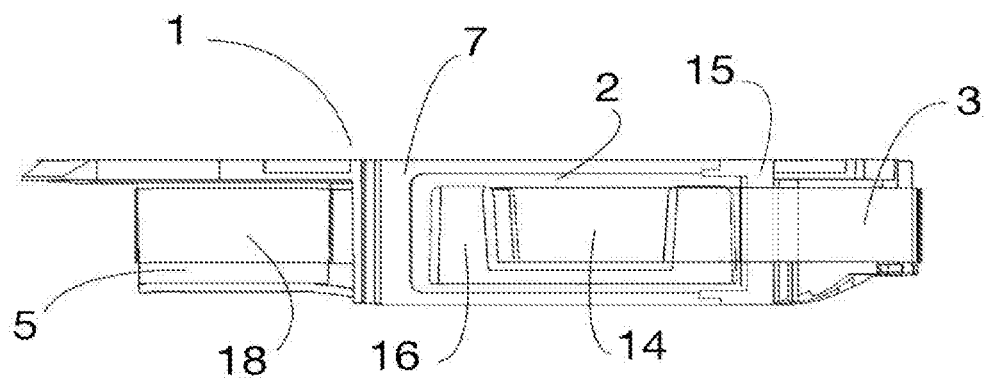
FIG. 6 is a schematic top view of a third embodiment diagnostic test unit for analysing body fluid with test tape exiting its storage chamber.

FIG. 6 depicts a housing (1) with test tape (3) exiting from a storage chamber (2) over a seal (15) that is integrated into the opening of storage chamber (2). Test tape (3) is drawn from storage chamber (2) by a drive (5) that can be either motor powered or manually turned, until a test zone is over a reading head (not shown) where a sample is applied for analysis. After analysis, used tests are stored on take up spool (18). Face (7) that borders the opening to storage chamber (2) provides a surface for the closing leaf spring with heat seal layer (19 not shown) to be heat welded, to seal storage chamber (2) protecting the unused test reel (14) and optional drying agent (16) contained therein. The spring may also be heat welded to the seal (15) but not the test tape (3) that lies over it.

Figure 7:
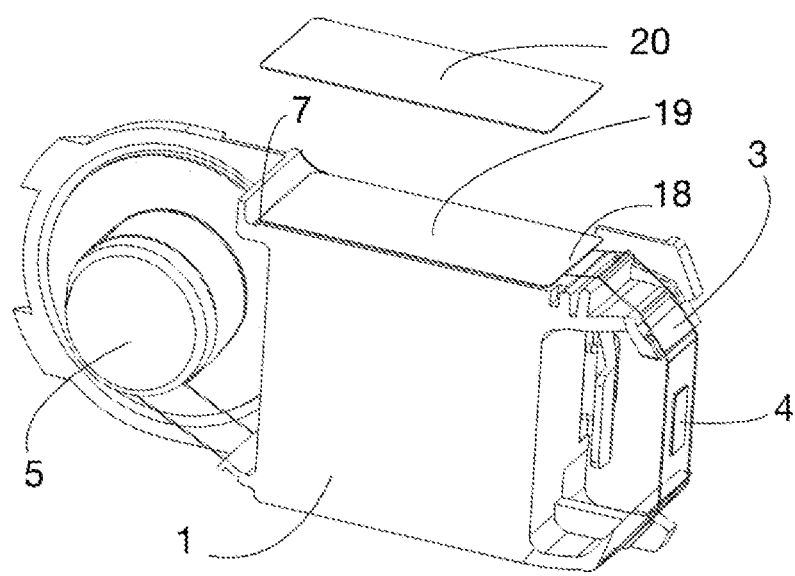
FIG. 7 is a schematic perspective view of the diagnostic test unit of FIG. 6 with a leaf spring with heat seal layer before heat welding and after heat welding over the storage chamber.

FIG. 7 shows a leaf spring with heat seal layer before heat welding (20) over storage chamber (2) after loading a roll of test tape and optionally a desiccant material. Leaf spring (19) applies downward force on the tape at the exit point (18) pressing the tape into the seal and forming a barrier that keeps the chamber isolated from the outside environment. The spring force applied to the tape depends on the degree of deflection of the spring which can be varied by adjusting the height of the seal relative to the face that borders the opening of the chamber (7). The spring is welded securely to the face (7) and optionally to the seal (15), but not to the tape or the seal directly under the tape. The spring (19) rises and falls at the exit point (18) as each test zone (11) exits, reducing the friction at the exit. Despite being a thin material, the spring does not transmit water vapour and so provides a shield against water ingress into the chamber.

Although the invention is described above in relation to preferred embodiments, it will be appreciated by those skilled in the art that it is not limited to those embodiments, but may be embodied in many other forms.

The invention claimed is:

1. A diagnostic tester for analyzing a body fluid, the diagnostic tester comprising: a test tape having test zones configured to receive the body fluid; a chamber configured to contain the test tape; a seal; an opening of the chamber which is at least partially bordered by the seal; a face on the chamber that borders the opening, at least part of the face being formed by the seal; a closing leaf spring in direct contact with the test tape and sealed onto the face, the closing leaf spring shielding the opening from an environment outside the chamber, the closing leaf spring being disposed in a plane in relation to a top of the seal so as to flex at the opening; and an exit gap formed between the closing leaf spring and the seal through which the test tape is configured to exit the chamber, wherein the closing leaf spring is sealed to the seal around an entirety of the opening except at the exit gap, and directly presses on the test tape at the exit gap to form a barrier that isolates the chamber from the environment outside the chamber.

2. The diagnostic tester according to claim 1, wherein the opening is configured for installation of a roll of the test tape through the opening into the chamber.

3. The diagnostic tester according to claim 1, wherein the test tape comprises:
   a carrier tape with test zones spaced at intervals; and
   a test zone-free area of carrier tape which is located in the exit gap during storage.

4. The diagnostic tester according to claim 1, wherein the chamber is part of a cassette, the test tape is configured to be moved out of a storage chamber via an application site into a waste chamber, and the exit gap is located proximate to the storage chamber.

5. The diagnostic tester according to claim 1, wherein the seal and closing leaf spring seal against the test tape.

6. The diagnostic tester according to claim 1, wherein a rear side of the test tape facing away from the test zones is configured to slide over the seal.

7. The diagnostic tester according to claim 1, wherein the closing leaf spring is composed of metal coated with a heat seal layer.

8. The diagnostic tester according to claim 7, wherein the closing leaf spring is composed of metal laminated with polypropylene.

9. A diagnostic tester for analyzing a body fluid, the diagnostic tester comprising: a plurality of test strips, each having at least one test zone configured to receive the body fluid; a chamber configured to contain the plurality of test strips; a seal; an opening of the chamber that is at least partially bordered by the seal; a face on the chamber that borders the opening, at least part of the face being formed by the seal; a closing leaf spring sealed onto the face and configured to directly contact the plurality of test strips, the closing leaf spring shielding the opening from an environment outside the chamber, the closing leaf spring being disposed in a plane in relation to a top of the seal so as to flex at the opening; and an exit gap formed between the closing leaf spring and the seal through which the plurality of test strips are configured to exit the chamber, wherein the closing leaf spring is sealed to the seal around an entirety of the opening except at the exit gap, and directly presses on the plurality of test strips at the exit gap to form a barrier that isolates the chamber from the environment outside the chamber.

10. The diagnostic tester according to claim 9, wherein the opening is configured for installation of the plurality of test strips into the chamber through the opening.

11. The diagnostic tester according to claim 9, wherein the chamber is part of a magazine, and the plurality of test strips are configured to be transported out of the chamber to an application site.

12. The diagnostic tester according to claim 9, wherein when the closing leaf spring is applied, the gap is formed.

13. The diagnostic tester according to claim 9, wherein the closing leaf spring is joined along a sealing line with the chamber or the seal.

14. The diagnostic tester according to claim 9, wherein the closing leaf spring is composed of spring steel having a heat-seal coating.

15. The diagnostic tester according to claim 9, wherein the seal is either (i) a single component injection-molded part or (ii) in combination with the chamber as a co-molded part composed of TPE (thermoplastic elastomer).

16. A diagnostic tester for analyzing a body fluid, the diagnostic tester comprising: a test tape with test fields for applying the body fluid; a chamber configured to contain the test tape; a seal; a closing leaf spring in direct contact with the test tape; a gap formed between the closing leaf spring and the seal, the gap being configured to allow passage of the test tape in use; and an opening of the chamber which is at least partially bordered by the seal, the opening being shielded from an environment outside the chamber by the closing leaf spring, and configured to act as a passageway for installing the test tape before the closing leaf spring is applied, wherein the closing leaf spring is disposed in a plane in relation to a top of the seal so as to flex at the opening, and the closing leaf spring is sealed to the seal around an entirety of the opening except at the gap, and directly presses on the test tape at the gap to form a barrier that isolates the chamber from the environment outside the chamber.

17. A diagnostic tester for analyzing a body fluid, the diagnostic tester comprising: a plurality of test strips, each with at least one test zone configured to receive the body fluid; a chamber configured to contain the plurality of test strips; a seal; an opening of the chamber that is at least partially bordered by the seal; a face on the chamber that borders the opening, at least part of the face being formed by the seal; a closing leaf spring sealed onto the face and configured to directly contact the plurality of test strips, the closing leaf spring being disposed in a plane in relation to a top of the seal so as to flex at the opening; and a gap formed between the closing leaf spring and the seal, the gap being configured to allow the plurality of test strips to be transported out of the chamber to an application site, wherein the opening is configured to allow the plurality of test strips to be installed before the closing leaf spring is applied, and the closing leaf spring is sealed to the seal around an entirety of the opening except at the gap, and directly presses on the plurality of test strips at the gap to form a barrier that isolates the chamber from an environment outside the chamber.

18. A portable device for analyzing a body fluid, the portable device comprising: a receiving bay configured to load a diagnostic tester, the diagnostic tester comprising: a plurality of test strips, each with at least one test zone configured to receive the body fluid; a chamber containing the plurality of test strips; a seal; a face on the chamber bordering the opening, at least part of the face being formed by the seal; a closing leaf spring sealed onto the face and configured to directly contact the plurality of test strips; a gap formed between the closing leaf spring and the seal, the gap being configured to allow passage of the plurality of test strips to an application site; and an opening of the chamber which is at least partially bordered by the seal, the opening being shielded from an environment outside the chamber by the closing leaf spring, the opening being configured to allow the plurality of test strips to be installed before the closing leaf spring is applied, wherein the closing leaf spring is disposed in a plane in relation to a top of the seal so as to flex at the opening, and the closing leaf spring is sealed to the seal around an entirety of the opening except at the gap, and directly presses on the plurality of test strips at the gap to form a barrier that isolates the chamber from the environment outside the chamber.

19. The diagnostic tester according to claim 15, wherein the seal is in combination with the chamber as the co-molded part composed of TPE (thermoplastic elastomer).

* * * * *